United States Patent
Hetzel et al.

(10) Patent No.: US 11,931,457 B2
(45) Date of Patent: Mar. 19, 2024

(54) THERAPEUTIC COMPOSITION FOR INTRAPERITONEAL ADMINISTRATION

(71) Applicant: CAPNOPHARM GMBH, Tübingen (DE)

(72) Inventors: Alexander Hetzel, Villingendorf (DE); Janek Kibat, Frankfurt am Main (DE); Ranjita Sahoo, Goch (DE); Mona Kibat, Munich (DE)

(73) Assignee: CAPNOPHARM GMBH, Tübingen (DE)

( * ) Notice: Subject to any disclaimer, the term of this patent is extended or adjusted under 35 U.S.C. 154(b) by 288 days.

(21) Appl. No.: 17/253,394

(22) PCT Filed: Jun. 24, 2019

(86) PCT No.: PCT/EP2019/066708
§ 371 (c)(1),
(2) Date: Dec. 17, 2020

(87) PCT Pub. No.: WO2020/002258
PCT Pub. Date: Jan. 2, 2020

(65) Prior Publication Data
US 2021/0267887 A1    Sep. 2, 2021

(30) Foreign Application Priority Data
Jun. 25, 2018 (EP) ..................... 18000556

(51) Int. Cl.
*A61K 9/12* (2006.01)
*A61K 9/00* (2006.01)
*A61K 31/704* (2006.01)
*A61K 33/243* (2019.01)

(52) U.S. Cl.
CPC .............. *A61K 9/12* (2013.01); *A61K 9/0019* (2013.01); *A61K 31/704* (2013.01); *A61K 33/243* (2019.01)

(58) Field of Classification Search
None
See application file for complete search history.

(56) References Cited

U.S. PATENT DOCUMENTS

| | | | | |
|---|---|---|---|---|
| 6,077,545 | A * | 6/2000 | Roskos ............... | A61K 47/42 424/649 |
| 2003/0147945 | A1 * | 8/2003 | Tardi ............... | A61K 31/7048 514/47 |
| 2011/0158983 | A1 * | 6/2011 | Bascomb ........... | A61K 39/3955 514/378 |

FOREIGN PATENT DOCUMENTS

| | | | |
|---|---|---|---|
| EP | 3427781 A2 * | 1/2019 | ............... A61J 1/10 |
| WO | 98/33486 A1 | 8/1998 | |

OTHER PUBLICATIONS

Karbownik et al (Wspolczesna Onkol, 2012, 16(5), 435-439) (Year: 2012).*
Beijnen et al (International Journal of Pharmaceutics, 32, 1986, 123-131) (Year: 1986).*
Clemens et al., 2015, (https://www.clinicaltrials.gov/ct2/show/NCT02475772?term=PIPAC&draw=3&rank=41) (Year: 2015).*
International Search Report and Written Opinion dated Sep. 10, 2019 for corresponding PCT Application No. PCT/EP2019/066708.
Giorgi Nadiradze et al., "Pressurized Intraperitoneal Aerosol Chemotherapy (PIPAC) with Low-Dose Cisplatin and Doxorubicin in Gastric Peritoneal Metastasis," Journal of Gastrointestinal Surgery, vol. 20, No. 2, 2015, pp. 367-373 XP035943085.
Wiebke Solass et al., "Intraperitoneal Chemotherapy of Peritoneal Carcinomatosis Using Pressurized Aerosol as an Alternative to Liquid Solution: First Evidence for Efficacy," Annals of Surgical Oncology, vol. 21, No. 2, 2013, pp. 553-559 XP055526769.
Tanja Khosrawipour et al., "Pressurized Intra Peritoneal Aerosol Chemotherapy in patients suffering from peritoneal carcinomatosis of pancreatic adenocarcinoma," PLOS ONE, vol. 12, No. 10, 2017, p. e0186709 XP055526775.
Clemens B. Tempfer et al., "A phase I, single-arm, open-label, dose escalation study of intraperitonela cisplatin and doxorubicin in patients with recurrent ovarian cancer and peritoneal carcinomatosis," Gynecologic Oncology, vol. 150, No. 1, 2018, pp. 23-30 XP085410899.

* cited by examiner

Primary Examiner — Celeste A Roney
(74) Attorney, Agent, or Firm — POLSINELLI PC

(57) ABSTRACT

The present invention refers to a set for the production of a ready-to-use chemo-therapeutic composition for intraperitoneal administration as an aerosol, wherein the set comprises an aqueous concentrate containing at least cisplatin in a first predetermined concentration and doxorubicin in a second predetermined concentration with a predetermined ratio of the first and the second concentration and having a pH value in the range from 3.0 to 7.0. The set further comprises a physiological aqueous carrier solution, which is for optional dilution of the concentrate depending on target concentrations of cisplatin and doxorubicin in the chemo-therapeutic composition to be applied. Further, the invention refers to a method for providing of a ready-for-use chemotherapeutic composition for intraperitoneal administration as an aerosol by using of a set, to a chemotherapeutic composition for intraperitoneal administration as an aerosol, and a use of the chemotherapeutic composition.

17 Claims, 1 Drawing Sheet

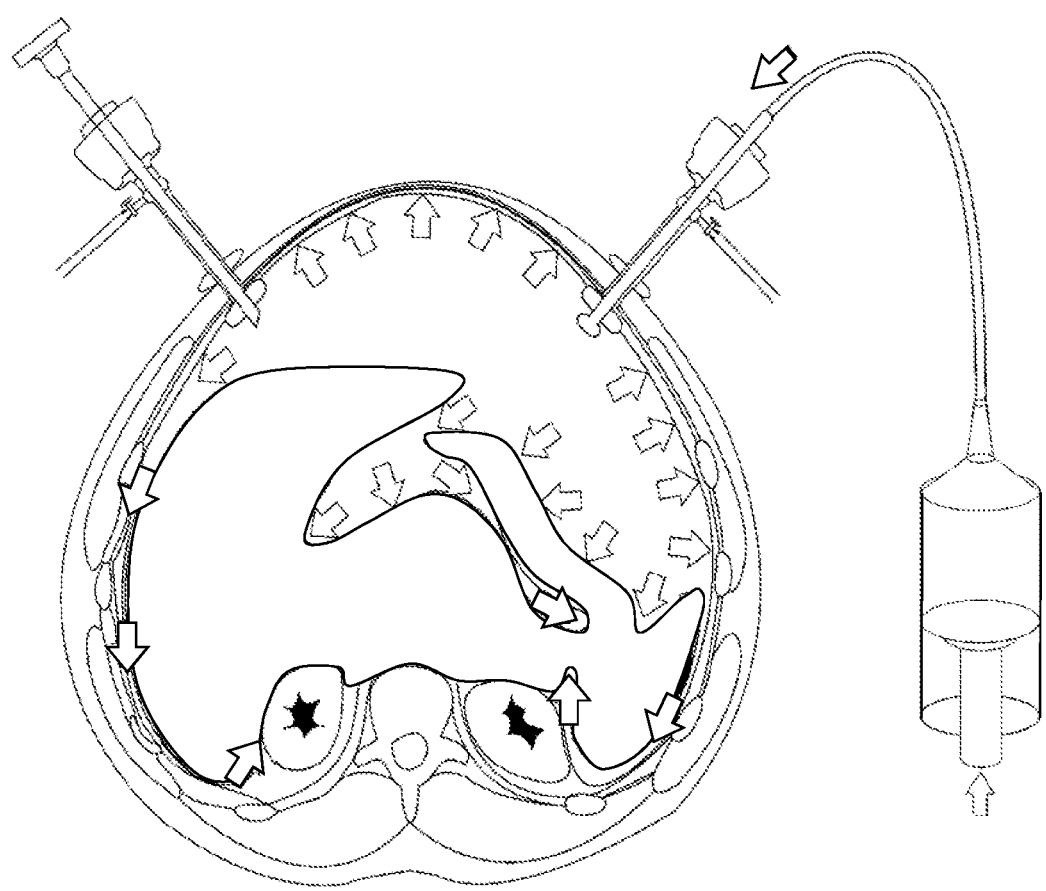

THERAPEUTIC COMPOSITION FOR INTRAPERITONEAL ADMINISTRATION

CROSS-REFERENCE TO RELATED APPLICATIONS

This application is a national stage application (under 35 U.S.C. § 371) of PCT/EP2019/066708, filed Jun. 24, 2019, which claims benefit of European Application No. 18000556.3, filed Jun. 25, 2018, which are incorporated herein by reference in their entireties.

The invention relates to a therapeutic composition for intraperitoneal administration in the form of a clear solution to be applied in the form of an aerosol, as well as to a method and a set for the provision thereof. The invention also relates to the use of the therapeutic composition for administration as an aerosol by using a medical device.

A well-known drug, cisplatin (cis-diamminedichloroplatinum, CDDP) is used as a cytostatic agent mainly for treatment of testicular, ovarian, bronchial, bladder and cervical carcinomas, squamous cell carcinomas on head and neck as well as chorionic carcinomas. Usually, cisplatin is used by administration by infusion in this context. Generally, infusions are time consuming and use additional diluents. For example, intravenous infusions last over several hours, up to 92 h, and are to be administered repeatedly, every week or every second week. The IV infusions require a special central venous port comprising surgical procedure with risks of infection, thrombosis and dysfunction. Further, there is a risk of extravasation of chemotherapeutic drugs inducing tissue necrosis. Thereby, higher doses lead to higher organ toxicity and higher side-effects of therapy, whereas less drug reaches the target organ, which is the peritoneum or pleura in the present application. Due to requirement of higher doses the costs increase of complete therapy. Administration of IV infusions may take place only on surveillance by certified physician. After all, repeated safety controls (e.g. blood sampling) and monitoring are necessary because of toxicity.

Due to the low solubility in water, the cisplatin concentrations that can be attained in infusion solutions are limited, because larger particles, such as arising in a suspension at higher concentrations, need to be prevented in order to prevent the blood vessels from clogging. There are limitations of drug dose administered via IV due to burden on liver and spleen.

Intraperitoneal or intralesional administration open new doors to drug therapy, due to possibility of using drugs at higher concentrations, modulation of drug penetration profile depending upon the type of formulations used, low to minimal risk clogging of blood vessels. Intraperitoneal drug administration route provides direct access to key organs and is a potential option to target drugs at specific sites.

Referring to a direct intralesional injection, DE 696 21 942 T2 describes a cisplatin formulation comprising 2 to 8 mg/ml cisplatin powder in aqueous dispersion and 0.05 to 0.75% of a non-ionic surfactant in a gel matrix. A gel formulation disclosed in said reference for the release of cisplatin to a neoplastic lesion comprises 1.5 to 6.5 mg/ml cisplatin powder, 0.05 to 0.75% polysorbate 80 as surfactant, 0.05 to 0.2 mg/ml epinephrine, 0.5 to 5% (wt/vol) collagen and, if applicable, 0.01 to 0.25% carboxymethylcellulose-sodium in an aqueous vehicle.

Another problem associated with aqueous cisplatin solutions is the low stability resulting from decomposition of the cisplatin complex. An improvement of the stability can be attained by lowering the pH value to pH 2 to 3 using hydrochloric acid. For reducing the detrimental consequences associated with the administration of solutions that are this acidic, U.S. Pat. No. 4,889,724 discloses a cisplatin solution with a composition comprising 0.1 to 1.0 mg/ml cisplatin, 9 to 15 mg/ml NaCl, and 0.025 to 0.075 mg/ml citric acid for adjustment of the pH to approximately 3 to 4.

However, administration of cytotoxic therapeutic solutions at these low pH values is associated with unnecessary additional and unspecific toxicity for unaffected, healthy target organ, in particular chemical peritonitis/serositis, which in turn induces acute abdominal pain, peritoneal inflammation and peritoneal fibrosis or sclerosis as the consequence of repeated exposition of the serosa to non-physiological substances. This has been extensively studied in chronic peritoneal dialysis, where initial, non-physiological solutions were poorly tolerated and induce severe peritoneal sclerosis (SPS), in some cases a deadly disease.

Moreover, it is known from the prior art of using chemotherapeutic agents that intraperitoneal chemotherapy delivery is associated with disabling locoregional side-effects, including severe abdominal pain, infection and bowel perforations. Current knowledge is that this local toxicity is dose-dependent. Against this framework, administering chemotherapy in the form of an aerosol under pressure intraperitoneally allows to reduce the dose administered without loss of efficacy. PIPAC (pressurised intraperitoneal aerosol chemotherapy) for the treatment of tumours in the abdominal cavity, e.g. of intraperitoneal metastases has been shown in a systematic, evidence-based review to be safe and well tolerated ("Systematic Review of Pressurized Intraperitoneal Aerosol Chemotherapy for the Treatment of Advanced Peritoneal Carcinomatosis", Grass et al., British Journal of Surgery, 104 (6), 2017).

During PIPAC, a chemotherapeutic agent is nebulised in the abdominal cavity by means of a laparoscopic intervention, whereby a better therapeutic index, which indicates efficacy vs. toxicity, i. e. local vs systemic concentration of the chemotherapeutic agent, in the tumour can be attained than with systemic administration.

As is evident from published studies, a relatively new treatment method involves the initial introduction under pressure into the abdominal cavity of an aerosol containing cisplatin at an escalated dosage of 10.5 mg/m$^2$ body surface area, with respect to current dosages of 7.5 mg/m$^2$ body surface area, in 150 ml of a 0.9% NaCl solution, followed by an aerosol containing doxorubicin at a escalated dosage of 2.1 mg/m$^2$ body surface area, with respect to current dosages of 1.5 mg/m$^2$ body surface area, in 50 ml of a 0.9% NaCl solution ("A phase I, single-arm, open-label, dose escalation study of intraperitoneal cisplatin and doxorubicin in patients with recurrent ovarian cancer and peritoneal carcinomatosis", Tempfer et al., Gynecol Oncol., 2018 May 6, pii: S0090-8258(18) 30851-5).

With PIPAC, no significant tissue fibrosis is observed ("Peritoneal Metastasis From Pancreatic Cancer Treated With Pressurized Intraperitoneal Aerosol Chemotherapy (PIPAC)", M Graversen et al., Clin. Exp. Metastasis, 34 (5), 309-314. 2017 May 17), due to micronization with droplet sizes around 30 μm. With hydrostatic pressure applied, deeper tissue penetration (as compared to liquids) and higher tissue drug concentration can be achieved.

A further aspect refers to high flow drug delivery system. Drug transfer occurs as diffusion (small molecules) or convection (large molecules). For intraperitoneal chemotherapy, large molecules are used that remain longer within the peritoneal cavity. As an unwanted effect, tissue penetration is low with large molecules, which are not transported by diffusion. During PIPAC, fluid is "pressed" into the tissue leading to oedema of the subperitoneal tissue (Jacquet P, Stuart O A, Chang D, Sugarbaker P H., "Effects of intra-abdominal pressure on pharmacokinetics and tissue distribution of doxorubicin after intraperitoneal administration", Anticancer Drugs 1996; 7: 596-603; Jacquet P, Sugarbaker P H. "Clinical research methodologies in diagnosis and staging of patients with peritoneal metastasis" in: Peritoneal Metastasis: Principles of Management (ed. Sugarbaker P H). Boston: Kluwer Academic Publishers, 1996. pp. 359-74). Thus, PIPAC can enhance convective tissue uptake of chemotherapeutic drugs.

Based on said prior art, it is the object of the present invention to provide an improved chemotherapeutic composition for treatment of carcinomas in the abdominal cavity by means of an intraperitoneal administration in the form liquid solution for an aerosolised application that comprises improved storage stability combined with a simplified user-friendly application and improved occupational safety for the person administering the treatment, e.g. the physician.

Said object is met by a set having the features of claim 1.

The further object, being the generation of a chemotherapeutic composition from the set, is met by the method having the features of independent claim 9.

A further object of the present invention is the provision of an improved chemotherapeutic composition for treatment of carcinomas in the abdominal cavity by means of an intraperitoneal administration in the form liquid for an aerosol that is associated with less local toxicity and adverse effects for the patient as described above with conventional treatments like IV infusions etc.

Said object is met by a therapeutic composition having the features of claim 12.

A use of the chemotherapeutic composition is disclosed with the features of claim 13.

Embodiments are described in the dependent claims.

A first embodiment of the set according to the invention for the production of a ready-to-use chemotherapeutic composition for intraperitoneal administration in the form of liquid to be aerosolised comprises an aqueous concentrate containing at least cisplatin in a first predetermined concentration and doxorubicin in a second predetermined concentration with a predetermined ratio of the first and the second concentration and having a pH value in the range from 3.0 to 7.0. In the aqueous concentrate, cisplatin and doxorubicin may be diluted with diluents of aqueous nature (pH 3 to 7.0) containing mainly water for injection (WFI) and sodium chloride, optional surfactants, buffer, salts, emulsifiers, polymers individually or in combination.

Furthermore, the set may comprise a physiological aqueous carrier solution, which is for optional diluting the aqueous concentrate. For practical reasons, in the set each of the concentrate and the physiological aqueous carrier solution preferably may be provided in predetermined volumes, wherein the volume of the carrier solution complies with the volume of the concentrate, which usually is applied completely, in a way that diluting of the concentrate with the complete volume of the carrier solution results in a composition with lowest possible target concentrations which may be administered. So, dilution volumes of the carrier solution depend on target concentrations of cisplatin and doxorubicin in the chemotherapeutical composition to be produced with the set. Therefore, there may be cases, where the concentrate of the set may be used without dilution. The inventive set provides the aqueous concentrate with fixed concentrations of at least cisplatin and doxorubicin in a given volume, which is adequate for wide diverse group of patients, and the physiological aqueous carrier solution in a given dilution volume. Thereby, the set offers a variety of chemotherapeutic compositions simply by adjusting the dilution volume of the carrier solution which is added to the concentrate, i. e. from pure concentrate (dilution volume added=0) to solution with lowest possible concentrations (complete dilution volume added).

It should be noted that a set according to an embodiment of the invention may comprise solely the aqueous concentrate, since a physiological carrier solution, which is for optional dilution of the concentrate, may be available in the clinical facilities, where the chemotherapeutic composition is to be administered by a physician.

Surprisingly, it has been found that pH value of the aqueous concentrate depends on preparation procedure, i. e., the order of solving the solid matter, i. e. cisplatin and doxorubicin and optionally further cytostatic agents, and mixing thereof. With a first preparation procedure, comprising mixing of the solid matter, cisplatin and doxorubicin, and solving of the mixed solid matter together in aqueous solvent for obtaining the aqueous concentrate, the resulting pH value of the aqueous concentrate is in acidic range, whereas a second preparation route, which comprises separate solving of cisplatin and doxorubicin in aqueous solvent before mixing of both solutions for obtaining the aqueous concentrate, results in a pH value in a neutral range of the aqueous concentrate. Even more surprising, the aqueous concentrate, which has been obtained by the second preparation route, is stable for at least several weeks without decomposition of cisplatin complex though having a pH value in the neutral range. So, a set according to an embodiment of the invention comprising such an aqueous concentrate of at least cisplatin and doxorubicin, having a pH value in a neutral range enables production of the ready-to-use chemotherapeutic composition for intraperitoneal administration in the form of liquid to be aerosolised without the negative side effects connected with low pH values as described above. However, there may be cases, where an acidic pH value of the concentrate may be preferred. By appropriate selection of the preparation route the resulting aqueous concentrate can be provided with a pH value in a desired pH range, wherein additional pH modifiers and/or buffering agents for pH adjustment can provide additional stability.

The predetermined ratio of the first and the second concentration is set according to a given therapy plan for a definite health related condition including prevention or treatment of various kinds of solid tumours, for example gynaecological, gastrointestinal, pulmonary or urological cancers. Such therapy plans and therefore the predetermined ratio of the concentrations may vary with advance in medical research. Therefore, the predetermined ratio of cisplatin concentration and doxorubicin concentration may be set in a range from 20:1 to 1:20, for example. A preferred predetermined ratio may be in a range from 15:1 to 1:15, and more preferred 12:1 to 1:12. A ratio of the first and the second concentration corresponding to currently applied dosages may be around 5:1.

Thereby, the first predetermined concentration of cisplatin in the concentrate may be in a range from 0.50-1.00 mg/ml, preferred 0.5-0.85 mg/ml, most preferred around 0.5-0.75 mg/ml. The second predetermined concentration of doxorubicin in the concentrate may be in a range from 0.05-0.5 mg/ml, preferred 0.09-0.3 mg/ml, most preferred around 0.1-0.2 mg/ml.

The set enables a form of cisplatin in the concentrate that is stable on storage, comprises a pH ranging from 3.0 to 7 and concurrently provides a pre-produced fixed combination of the chemotherapeutic agents cisplatin and doxorubicin such that the attending person and/or physician can combine the concentrate and the carrier solution in one step prior to the administration in the form as an aerosol- and no longer needs to prepare two treatment solutions, as is the case thus far-in order to be able to administer both chemotherapeutic agents. This lowers the risk for the attending person handling the toxic chemotherapeutic agents considerably as well as it lowers the preparation time of therapy and reduces waste generated.

The preparation of the fixed drug combination in a single syringe also simplifies aerosolization in the operating room with a dedicated, industry-standard angio-injector since it is not necessary anymore to exchange the first syringe (e. g. containing doxorubicin) with a second syringe (e.g. containing cisplatin). This shortens the applications time and reduces the risk of environmental contamination.

Finally, the preparation of the fixed drug combination in a single syringe allows to wash out the dead volume of the injection system (consisting of the syringe placed into the angio-injector, a up to 5 meter long high-pressure line and the aerosolizer itself) with saline solution an therefore to achieve a high reproducibility of the dose distributed to the patient. As an embodiment, this wash-out is possible without en-tering the operating room when a double-head angio-injector is used.

The concentrate of the set already provides a desired predetermined ratio of the concentrations of cisplatin and doxorubicin to the therapeutic composition that is obtained by optional diluting with the physiological carrier solution like saline, or other etc, or alternatively with suitable diluent as described below. If the concentrate is applied as therapeutic composition without dilution, the pH of the therapeutic composition corresponds to the pH value of the concentrate, which is in the range from 3.0 to 7.0. By diluting the concentrate, the desired target concentration is set and a target pH value of the chemotherapeutic composition is attained that may be in the range from 3.0 to 7.0, too, but preferably may be shifted to less acidic values for better tolerance by the patient.

In an embodiment of the set, the concentrate may contain at least a third cytostatic agent in a third concentration with a predetermined ratio in relation to the first and the second concentrations.

The cisplatin-stabilisation is established through the addition of suitable pH modifier or buffering agent individually or in combination of them. Suitable pH modifi-ers/buffering agents may be hydrochloric acid, citric acid, acetic acid and/or glycine. An appropriate amount for adjusting the pH value depends on the desired pH value to be adjusted and is preferably in a range of 0.001 to 5 mg/ml. Citric acid can be preferred in this context due to its better tolerability and formulation stability. In order to set a pH of 3.5, e. g, in the concentrate, citric acid can be used at a concentration of approximately 0.001 to 0.5 mg/ml (preferably 0.5 mg/ml). Other acidifying agents like hydrochloric acid, acetic acid, and carboxylic acid can be used preferably in ranges 0.001 to 0.3 mg/ml.

In a preferred embodiment, the concentrate of the set according to the invention may further comprise at least one of an emulsifier and polymer. In particular, the concentrate may comprise a water soluble polymer, inactive carrier, emulsifier, surfactant for the function selected and/or as a gelling agent, thickening agent and/or emulsifying agent, selected from the group comprising hyaluronic acid, gel-Ian, poloxamer. Polymer can be used to set the viscosity of the composition that can be produced through the addition of the carrier solution of the set according to the invention in order to attain optimal wetting of the peritoneum in the abdominal cavity by the aerosol. The viscosity of the composition to be set lies in a range from 1 to 100 mPas and preferred from 1 to 30 mPas. Wetting is important since the substance transport of the chemotherapeutic agents into the cells does not pro-ceed by diffusion, but rather by convection, whereby the carrier solution taken up by the tissue carries along the dissolved substances.

The water-soluble polymer may be present in a range from 0.1 to 10 wt %, preferred 0.5 to 5 wt %; the gelling agent may be present in a range from 0.1 to 5 wt %, preferred 0.1 to 3 wt %, and the thickening agent may be present in a range from 0.1 to 5 wt %. The emulsifying agent or surfactant may be present in a range from 0.1 to 3 wt %.

The physiological aqueous carrier solution preferably is an isotonic aqueous solution containing 0.9% (wt/vol) NaCl, i.e. 0.9 g NaCl per 100 ml of solution optionally with adjusted pH using suitable buffering agent or pH modifier. However, the physiological aqueous carrier solution may be selected from any other suitable diluent solutions. If applicable, for example for use in patients suffering from hypernatremia, a carrier solution may contain 5% (wt/vol) glucose, i.e. 5 g glucose per 100 ml of solution. Further physiological additives may be lactose or mannitol; the different physiological additives may be applied individually or in combination of them.

A method according to the invention for the production of a ready-for-use chemo-therapeutic composition in the form of liquid solution for aerosolised administration uses a set according to the invention and comprises the steps of:

providing an aqueous concentrate containing at least cisplatin in a first predetermined concentration and doxorubicin in a second predetermined concentration with a predetermined ratio of the first and the second concentration and having a pH value in the range of 3.0 to 7.0, setting target concentrations of cisplatin and doxorubicin in the predetermined ratio in the chemotherapeutic composition as a function of a predetermined patient body surface area, and—after comparing of the predetermined concentrations with these target concentrations of cisplatin and doxorubicin—adjusting these target concentrations, and in case these target concentrations deviate from the first and second concentrations mixing a physiological aqueous carrier solution with the concentrate at a predetermined mixing ratio which depends on a target concentration of cisplatin and doxorubicin, whereby the chemotherapeutic composition is obtained.

The chemotherapeutic composition having the target concentrations comprises cisplatin and doxorubicin with the predetermined ratio and having a pH value in the range of 3.0 to 7.0 in the target concentrations, which were determined as a function of the patient body surface area. Hereby, this patient body surface area may be any body surface area of an arbitrary patient intended to receive administration of a predetermined dosage of the chemotherapeutic composition.

A predetermined dosage of the chemotherapeutic composition having the target concentrations may be 10.5 mg/m$^2$ body surface area of cisplatin and 2.1 mg/m$^2$ body surface area of doxorubicin, for example.

In particular, the predetermined mixing ratio may be set by measuring a volume of the physiological aqueous carrier solution which is be added to a given volume of the concentrate. The predetermined mixing ratio includes the case, wherein the volume of the physiological aqueous carrier solution may be 0, if the concentrate is to be administered undiluted.

Therefore, the set may provide the aqueous concentrate in a given volume adequate for a body surface area of, for example, 2.5 m$^2$ and a volume of carrier solution adapted for providing therapeutic compositions suitable for a wide diverse group of patients depending on their actual body surface by enabling a variety of mixing ratios. For example, the aqueous concentrate in the set may be provided with a 40 ml dosage containing 0.656 mg/ml cisplatin and 0.131 mg/ml doxorubicin, and up to 200 ml dilution volume of carrier solution, which optionally is to be mixed partially or completely with the concentrate according to the target concentrations which depend on respective body surface areas for obtaining the therapeutic composition.

Accordingly, the exemplary actual dosage exceeds the previously used dosage of 7.5 mg/m$^2$ body surface area of cisplatin and 1.5 mg/m$^2$ body surface area of doxorubicin for intraperitoneal administration as an aerosol in order to attain an improved effect, but still is far below the concentration of the intralesional gel formulation from the prior art ranging from 1.5 to 6.5 mg/ml of cisplatin powder in order to prevent any damage to the healthy tissue.

It is noted that the set according to an embodiment of the invention is not limited to the example given above. It is clear that an inventive set may comprise the concentrate with a given volume and the carrier solution with a dilution volume that may vary from above exemplary values, as well as the concentrations in the concentrate may differ from the values indicated above.

In a preferred embodiment of the method the provision of the aqueous concentrate comprises selecting a preparation procedure thereof depending on the desired pH value, wherein a first preparation procedure comprises adding of both, cisplatin and doxorubicin, together to aqueous solvent, i. e. mixing the solid matter before solving, resulting in a pH value in acidic range, and wherein a second preparation route comprises separate solving of cisplatin and doxorubicin in aqueous solvent before mixing both solutions, preferably by adding both solutions in a predetermined dilution amount of aqueous solvent, resulting in a pH value in a neutral range. By appropriate selection of the preparation route resulting in a desired pH range, additional pH modifiers and or buffering agents for pH adjustment can be for further stabilisation. The second preparation procedure resulting surprisingly in a stable concentrate having a pH in neutral range may be preferred, since administration thereof may comprise less negative side effects connected with low pH values as described above. However, there may be cases, where an acidic pH value of the concentrate, and therefore the first preparation procedure, may be preferred or alternatively use of pH modifiers is recommended.

A chemotherapeutic composition according to the invention that is suitable and intended for intraperitoneal administration as a liquid to be aerosolised, is produced from a set according to the invention and correspondingly comprises at least cisplatin and doxorubicin at the predetermined concentration ratio in a physiological aqueous carrier solution and has a pH value in the range from 3.0 to 7.0. Thereby, the target concentrations in the chemotherapeutic composition, which are determined as a function of the patient body surface area, are adjusted by optional dilution of the concentrate with a physiological aqueous carrier solution, in case the target concentrations deviate from the first and the second predetermined concentrations.

Furthermore, the composition may comprise pH modifiers and/or buffering agents, selected from a group comprising hydrochloric acid, citric acid, acetic acid, and glycine for setting the pH value. Further components of the composition comprise a least one of emulsifier and polymer solution; wherein a water-soluble polymer may be present in a range from 0.1 to 10 wt %, preferred 0.5 to 5 wt %; the gelling agent may be present in a range from 0.1 to 5 wt %, preferred 0.1 to 3 wt %, and the thickening agent may be present in a range from 0.1 to 5 wt %. The emulsifying agent or surfactant may be present in a range from 0.1 to 3 wt %. Polymers may be selected from the group comprising hyaluronic acid, gellan, poloxamer as gelling agent, thickening agent and/or emulsifying agent for setting the viscosity for optimized aerosolizing.

The composition according to the invention that combines cisplatin and doxorubicin in an aqueous carrier solution can be used not only for effective treatment of carcinomas in the abdominal cavity by intraperitoneal administration as an aerosol at a dosage that is low as compared to systemic administration, but this composition, in which approximately 5 to 15% of a systemic dose are administered, can also be used for prophylactic treatment after removal of a carcinoma in the abdominal cavity in order to minimise the risk of metastasis due to the improved therapeutic index, i.e. improved effect associated with fewer undesired effects and/or lower toxicity.

In an embodiment, the composition according to the invention can comprise fixed concentrations of at least cisplatin and doxorubicin in the aqueous carrier solution at a pH value of 3.0 to 7.0, for providing a standard dosage with a fixed application volume. The fixed concentrations may be selected on basis of a mean body surface (corresponding to percentile 50 in the general population). Such a standard dosage might be an alternative option since peritoneal surface does not change with body weight although patients are losing weight before treatment and most of them the gaining weight under chemotherapy. Another approach for applying the application dosage of 10.5 mg/m$^2$ body surface area of cisplatin and 2.1 mg/m$^2$ body surface area of doxorubicin using the composition with fixed concentrations may comprise varying of the application volume depending on the body surface area. However, adjustment of the concentrations in a fixed application volume depending on the body surface area by adjusting a mixing ratio of concentrate and carrier solution is the preferred application route.

An inventive use of the chemotherapeutic composition comprises generating of an aerosol which is intended for administration into a gas-expanded body cavity or hollow organ of a patient, wherein the chemotherapeutic composition is sprayed by means of a nozzle which is introduced into a trocar which is intended for ex-tending into the gas-expanded body cavity or hollow organ of the patient. Such intraperitoneal administration may involve a nozzle that merges into a trocar sleeve that is intended for introduction of an insufflation gas into the abdominal space of a patient. According to definition, an aerosol is a fine distribution of liquid or solid substances or carrier substances (airborne particles, typically in particle size range between 1 nm to 100 um) in gas, presently in the insufflation gas.

The use of the chemotherapeutic composition may be intended for preventing or treating various kinds of solid tumours, for example gynaecological, gastrointestinal, pulmonary or urological cancers.

Thereby, the aerosol may be generated by means of dual-component aerosolizing devices with continuous gas flow or electro spraying devices.

Further objects and advantages of the embodiments of the present invention will be readily appreciated and become better understood by reference to the following more detailed description of preferred embodiments in connection with the drawing:

The only FIGURE (FIG. 1) shows a cross-section of a gas-expanded body cavity filled with aerosol of an inventive composition administered by an aerosolizing device.

In the example of FIG. 1, a therapeutic composition according to the invention is administered in pressurized intraperitoneal aerosol chemotherapy into a hollow space 3 or body cavity 3 that is already expanded by carbon dioxide, for example, at a pressure between 6 and 30 mm Hg, routinely between 12 and 15 mmHg. For generating of the gas-expanded body cavity 3, inflating gas is introduced viaduct 4 of a first trocar A by means of a micropump 5. After body cavity 3 is inflated, the therapeutic composition which is provided in dosage device 6 having a high pressure (ca. 1.500 kPa) injector 7 is then aerosolised into the body cavity 3 by means of a device 10 which is introduced through first trocar A. A second trocar B comprising a video monitoring device 9 is installed and connected to a closed line 8 for exhausting safely the toxic therapeutic aerosol at the end of the procedure. The trocar system can just as well comprise additional trocars.

In this context, one of the two or both trocars comprise an inlet for the therapeutic composition that communicates with a reservoir of the therapeutic composition and has a nozzle for nebulisation of the therapeutic composition arranged on its distal end.

An essential feature of the therapeutic composition according to the invention, which, advantageously, can be produced readily from the set according to the invention in just a single step and therefore is associated with less risks for the user, is the ability, provided thereby, to administer the at least two chemotherapeutic agents concurrently in combination such that a predetermined concentration ratio of cisplatin and doxorubicin of 5:1, for example, is in fact attained throughout the abdominal space, which is not ensured upon sequential administration. Thereby, application of the at least two chemotherapeutic agents is easier, since only one administration is necessary. So, in contrast to conventional application of the two chemotherapeutic agents, administration of the inventive composition requires only a single aerosolization phase, resulting further in reduced duration or sittings of treatment as well as reduced costs. Apart from the drug combination effect with consistent distribution of both all over the inflated body cavity, the aerosolised form of the composition gives better drug availability at tumour site.

The concept of having a set with a concentrate containing the at least two cytostatic agents cisplatin and doxorubicin and optional further cytostatic agents simplifies the application for the attending person, who simply needs to mix the concentrate with the inert carrier solution e.g. saline, glucose solution etc. for the administration. Cisplatin and doxorubicin are being administered to the patient jointly and in a single application such that the duration of treatment may be reduced considerably.

The following table compares currently used clinical solutions with an inventive example:

| Currently used Clinical solutions | example according to an embodiment of the invention |
|---|---|
| Concentrations are calculated for surface area 1.8 m² | Concentrations of concentrate are calculated for surface area 2.5 m², therefore suitable for wide diverse group of patients |
| In procedure, 150 ml CIS (Cisplatin) solution is administered followed by 50 ml DOX (Doxorubicin) solution (in all 200 ml is administered to patient) | In procedure, 40 ml concentrate to be diluted to selected predetermined amount by doctors depending upon patient peritoneal surface area or concentrate can directly be directly used, e.g. for 2.5 m² surface area the concentrate to be directly diluted in 200 ml or less quantity of physiological solution. |
| Current doses administered: DOX dose 1.5 mg/m² CIS dose 7.5 mg/m² | Administration doses according to invention: DOX dose 2.1 mg/m² CIS dose 10.5 mg/m² |
| Currently: One drug is administered at a time followed by another drug | Product example according to an embodiment of the invention contains: Both drugs together as a combination product |
| DOX—2.7 mg in 50 ml saline CIS—13.5 mg in 150 ml saline | Recipe 40 ml: DOX 5.25 mg CIS 26.25 mg Saline solution q.s. to 40 ml Citric acid q.s to pH 3 to 7 surfactant q.s (extra optionally) Polymer q.s (extra optionally) |
| In therapy solution: DOX concentration—0.054 mg/ml CIS concentration—0.09 mg/ml | In concentrate: DOX concentration—0.131 mg/ml CIS concentration—0.656 mg/ml |
| Currently used drugs are in very diluted form (200 ml total) | Product example according to an embodiment of the invention is in concentrated form (40 ml) |
| pH 4.5 to 4.7 | pH 4.5 to 7.0 |
| Needs to be freshly prepared | Stable product |
| Therapy time: Solution preparation time + actual application time for pressurised intraperitoneal aerosol chemotherapy (PIPAC) 30 min | Therapy time: application time for PIPAC procedure is less than 30 min: depending upon the volume of dilution; if concentrate is used as it is then less than 10 min |

In this example for an embodiment of the invention, the volume of 40 ml of the concentrate and recipe with indicated ingredients referring to this volume are exemplarily only. It is clearly understood that the scope of the invention is not limited to this volume of 40 ml and the indicated amounts of the ingredients in the example. The volume of the concentrate in the set according to the invention can be chosen appropriately and may range from 40 ml to 100 ml or preferably from 40 to 70 ml. However, it is not excluded that the volume of the concentrate may be less than 40 ml or higher than 100 ml. The amounts of the ingredients as well as the resulting concentrations of the chemotherapeutics may vary as well. The carrier solution may be provided in a volume of 200 ml, which is adequate for covering mixing ratios with the 40 ml concentrate resulting in concentration ranges in the chemotherapeutical compositions which are adapted for wide diverse group of patients. It is obvious that deviating volumes of the concentrate and/or deviating concentrations in the concentrate require deviating volumes of the carrier solution as well, in order to provide all necessary mixing ratios. So, the volume of the carrier solution may go below or exceed 200 ml depending on the volume and recipe of the concentrate.

The invention claimed is:

1. A set for producing a ready-to-use chemotherapeutic composition administered as an aerosol, the set comprising:

(a) a predetermined volume of an aqueous concentrate having a pH of 3.0 to 7.0, comprising 0.5 to 1 mg/ml of cisplatin and 0.09 to 0.5 mg/ml of doxorubicin, wherein the cisplatin and doxorubicin are solubilized in the aqueous concentrate;

wherein the aqueous concentrate is independently useable for administration as an aerosol that simultaneously delivers a target concentration of cisplatin and a target concentration of doxorubicin to a gas-expanded body cavity or hallow organ of a patient;

(b) optionally, a predetermined volume of a physiological aqueous carrier solution for diluting the aqueous concentrate when desired;

wherein (a) and (b), if present, are separately contained and (a) and (b) are combinable to form a liquid ready-to-use solution for administration as an aerosol that simultaneously delivers a target concentration of cisplatin and a target concentration of doxorubicin to a gas-expanded body cavity or hallow organ of a patient.

2. The set of claim 1, wherein the aqueous concentrate of (a) further comprises a third cytostatic agent other than the cisplatin and the doxorubicin.

3. The set of claim 1, wherein the pH value of the aqueous concentrate of (a) has been achieved by addition of a suitable pH modifier, buffering agent, or combination thereof.

4. The set of claim 3, wherein the pH modifier, buffering agent, or combination thereof comprises one or more of hydrochloric acid, citric acid, acetic acid, and glycine.

5. The set of claim 1, wherein the aqueous concentrate of (a) further comprises one or more emulsifiers, water-soluble polymers, or combination thereof.

6. The set of claim 5, wherein the aqueous concentrate of (a) comprises 0.1 to 3 wt. % of the one or more emulsifiers, based on a total weight of the aqueous concentrate.

7. The set of claim 5, wherein the aqueous concentrate of (a) comprises 0.1 to 10 wt. % of the one or more water-soluble polymers, based on a total weight of the aqueous concentrate.

8. The set of claim 1 comprising the predetermined volume of the physiological aqueous carrier solution of (b), wherein the physiological aqueous carrier solution comprises 0.9% (wt/vol) NaCl or 5% (wt/vol) glucose.

9. The set of claim 1, wherein the target concentration of cisplatin is about 0.5 mg/m$^2$ body surface and the target concentration of doxorubicin is about 2.1 mg/m$^2$ body surface area.

10. The set of claim 1, wherein the liquid ready-to-use solution is clear.

11. The set of claim 1, wherein the liquid ready-to-use solution has a pH of 3.0 to 7.0.

12. The set of claim 1, wherein the liquid ready-to-use solution has a pH of about 7.0.

13. A set for producing a ready-to-use chemotherapeutic composition administered as an aerosol, the set comprising:

(a) a predetermined volume of an aqueous concentrate having a pH of 3.0 to 7.0, comprising 0.5 to 1 mg/ml of cisplatin and 0.09 to 0.5 mg/ml of doxorubicin, wherein the cisplatin and doxorubicin are solubilized in the aqueous concentrate;

(b) a predetermined volume of a physiological aqueous carrier solution for diluting the aqueous concentrate;

wherein (a) and (b) are separately contained and (a) and (b) are combinable to form a liquid ready-to-use solution for administration as an aerosol that simultaneously delivers a target concentration of cisplatin and a target concentration of doxorubicin to a gas-expanded body cavity or hallow organ of a patient.

14. The set of claim 13, wherein the aqueous concentrate of (a) further comprises a third cytostatic agent other than the cisplatin and the doxorubicin.

15. The set of claim 13, wherein the aqueous concentrate of (a) further comprises one or more emulsifiers, water-soluble polymers, or combination thereof.

16. The set of claim 15, wherein the aqueous concentrate of (a) comprises 0.1 to 3 wt. % of the one or more emulsifiers, based on a total weight of the aqueous concentrate.

17. The set of claim 15, wherein the aqueous concentrate of (a) comprises 0.1 to 10 wt. % of the one or more water-soluble polymers, based on a total weight of the aqueous concentrate.

* * * * *